United States Patent [19]

Gardner et al.

[11] Patent Number: 4,534,787

[45] Date of Patent: Aug. 13, 1985

[54] N-L-SERYL-3-AZETIDINECARBOXYLIC ACID

[75] Inventors: Gary M. Gardner, Manteca; J. Edward Semple, Modesto, both of Calif.

[73] Assignee: Shell Oil Company, Houston, Tex.

[21] Appl. No.: 613,496

[22] Filed: May 24, 1984

[51] Int. Cl.³ .................... C07D 205/04; A01N 43/44
[52] U.S. Cl. ..................................... 71/88; 260/239 A
[58] Field of Search ..................... 260/239 AR; 71/88

[56] References Cited

FOREIGN PATENT DOCUMENTS 29265  6/1981 European Pat. Off. .
2312045  9/1974 Fed. Rep. of Germany .......... 71/88
2136903 12/1972 France .

OTHER PUBLICATIONS

Chen, et al, Bul. Chem. Soc. Jap., vol. 40(10), 1967, pp. 2398–2404.
Igarashi, et al, *Chem. Abstracts*, vol. 91, 1979, 56800g; 141178e.

Primary Examiner—Donald G. Daus
Assistant Examiner—William A. Teoli, Jr.

[57] ABSTRACT

N-L-seryl-3-azetidinecarboxylic acid, useful for sterilizing the male parts of plants.

5 Claims, No Drawings

N-L-SERYL-3-AZETIDINECARBOXYLIC ACID

BACKGROUND OF THE INVENTION

To obtain F₁ hybrid seeds, which have advantages over non-hybrid seeds, seed breeders cross-pollinate carefully selected parent plants. Wheat plants have hermaphroditic flowers, and normally self-pollinate. This characteristic can cause a problem in effecting cross-breeding, leading to mixtures of hybrid and non-hybrid seed. The problem has been solved in the past by emasculating (removing the male anthers of) each of the flowers of the prospective female parent plant by hand before it is pollinated with pollen from the prospective male parent. Such hand operations are extremely laborious and time-consuming, and require highly-skilled workers. Much research is being carried out with a view to effecting the emasculation by treating the prospective female parent with a chemical, and thus avoiding such hand operations.

DESCRIPTION OF THE INVENTION

It has now been found that N-L-seryl-3-azetidinecarboxylic acid selectively sterilizes the male parts of wheat plants by way of rendering the pollen grains non-functional—i.e., sterile. This azetidine derivative is described by the formula

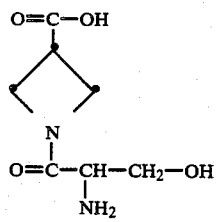

(I)

The present invention comprises this novel compound, a method for sterilizing the male parts of wheat plants, which method comprises applying to a wheat plant, prior to pollen shed, an effective amount of the compound, and a method for producing hybrid wheat seed which comprises applying to a candidate female parent wheat plant prior to pollen shed an effective dosage of the compound, causing the candidate female plant to be pollinated with pollen from a candidate male parent wheat plant, allowing the female parent to develop until the seed is mature, and harvesting the seed. The invention also includes compositions adapted for effecting these methods, which comprise an effective amount of the compound of Formula I, an inert carrier and a surface-active agent. The method according to the invention generally produces plants in which male sterility has been induced without an unduly adverse effect upon the female fertility of the plants. The treated plants thus are quite suitable for use in hybrid seed production.

It appears that the azetidine has the desired effect when it is applied to the plant at a time during the development of the pollen—i.e., between the time of floral initiation and pollen shed. Preferably, the azetidine is applied somewhat before the pollen is wholly mature, to ensure movement of an effective dosage of the azetidine into the concerned plant tissue, believed to be the pollen grains, in time to effect sterilization of the pollen. In wheat, this "application window" appears to extend from about growth stage 32 (second stem node detectable; anthers beginning to differentiate) to about growth stage 49 (awns appearing—i.e., late booting; pollen grains well developed). The definitions and meanings of the numbered growth stages are those set out by D. R. Tottman and R. J. Makepeace, Annals of Applied Biology, 93, 221-234 (1979).

The compound of Formula I is suitably applied at a dosage of from 0.25 to 15 kilograms per hectare, dosages of from 1.0 to 3.0 kilograms per hectare ordinarily sufficing.

The present invention also provides a method for producing F₁ hybrid seed which comprises cross-pollinating a wheat plant which has been treated with a compound of Formula I, according to the method of this invention, with pollen from a second untreated wheat plant.

The compound of Formula I will be formulated for use in the method of the invention. The invention, therefore, also provides a pollen-sterilizing composition which comprises the compound of Formula I, together with a suitable carrier and a suitable surface-active agent.

The term "carrier" as used herein means an inert solid or liquid material, which may be inorganic or organic and of synthetic or natural origin, with which the active compound is mixed or formulated to facilitate its application to the plant. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% to a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

In many, if not most, cases, the compound of Formula I is conveniently applied as a water solution containing a small amount of an inert surfactant, a nonionic material being suitable for the purpose. The surfactant of course must be a material that is not toxic to the plant to be treated, at the dosage of the azetidine which is to be used. In such compositions, the concentration of the compound of Formula I suitably is of the order of about 0.01 to about 1 percent by weight of the composition, while the concentration of surfactant is of the order of 0.05 to 2.0 percent (ordinarily about 0.1 to about 1.0 percent), on the same basis.

It is evident from the foregoing that this invention contemplates compositions containing as little as about 0.01% by weight to as much as about 75% by weight of a compound of Formula I as the active ingredient.

A method for preparing the compound of Formula I is described in the following example. The identity of each product mentioned in the example was confirmed by appropriate chemical and spectral analysis.

EXAMPLE 1

N-L-seryl-3-azetidinecarboxylic acid (1)

3-Azetidinecarboxylic acid was prepared by the method of Anderson & Lok (Journal of Organic Chemistry, 1972, Volume 37, pages 3953–7) as follows:

(a) 15 g of 1-(diphenylmethyl)-3-cyanoazetidine (Anderson and Lok) was mixed with 150 ml of 2-methoxyethanol and added to a solution of 13 g of potassium hydroxide in 10 ml of water. The resulting mixture was refluxed for 15 hours, during which time ammonia evolved, and then poured onto 1500 ml of ice and water. This mixture was then acidified with dilute hydrochloric acid until the pH was 1.5, and then extracted with dichloromethane. The aqueous phase was adjusted to pH 5 by addition of solid sodium bicarbonate. 1-diphenylmethyl-3-carboxyazetidine (1A) separated from the solution as a fine white solid. The solid was collected, washed with water and air-dried. M.p.: 190°–191° C. with decomposition. 10 g of 1A was suspended in 300 ml of methanol, and 6 g of a catalyst of palladium II hydroxide on charcoal, prepared by the method described in Tetrahedron Letters, 1967, page 1663, was added. The mixture was hydrogenated in a Parr apparatus at an initial hydrogen pressure of about 3.5 atmospheres absolute for 3 hours. Uptake of hydrogen stopped abruptly after 1 hour. The solution was filtered and evaporated almost to dryness under reduced pressure. The residue was extracted several times with dichloromethane and the combined extract phase was evaporated to dryness. The white solid residue was recrystallized from ethanol to give shiny plates of hydrated 3-azetidinecarboxylic acid, m.p.: 169°–170° C. with decomposition. Evaporation of the recrystallizing solvent gave a further crop of crystals, m.p. 235°–270° C. with decomposition. These crystals consisted of anhydrous 3-azetidinecarboxylic acid, and had an NMR spectrum identical to the hydrated acid.

15.0 g of thionyl chloride was added to a stirred solution of 5.06 g of 3-azetidinecarboxylic acid in 200 ml of dry methanol at 0°–5° C. under nitrogen, the addition occurring over a 30-minute period. The resulting solution was stirred at about 0° C. overnight, methanol and thionyl chloride were evaporated under reduced pressure, and the residue was held under very low pressure (<1 Torr.) for several hours to give the methyl ester hydrochloride of 3-azetidinecarboxylic acid (1B), as a colorless solid, m.p.: 86°–90° C.

3.37 g of triethylamine and 0.37 g of dimethylaminopyridine were added to a stirred mixture of 7.18 g of N-carbobenzyloxy-L-serine and 5.00 g of 1B in 150 ml of dry tetrahydrofuran at 0° C. under nitrogen. The stirred mixture was allowed to warm to about 5° C. (10 minutes), 6.19 g of N,N'-dicyclohexylcarbodiimide was added, heat being evolved, and the mixture was allowed to warm to 28° C. and held there (25 minutes). The mixture was stirred at room temperature over a weekend, when 3 ml of glacial acetic acid and 15 ml of methanol were added and the mixture was stirred at room temperature for 2.5 hours. Then sufficient triethylamine was added to make the mixture pH=7, the mixture was filtered and the solvents were evaporated from the filtrate under reduced pressure. The residue was mixed with 50 ml of methanol and 100 ml of ethyl acetate and filtered, and the solvents were evaporated from the filtrate under reduced pressure. The residue was flash-chromatographed, first with ethyl acetate as eluent to remove high $R_f$ minor impurities, then a 9:1 v:v mixture of ethyl acetate and methanol. The solvents were evaporated, the residue was recrystallized from methylene chloride and hexane, and the product was held under very low pressure (<1 Torr.) overnight to give the N-(N-carbobenzyloxy-L-seryl)-3-azetidinecarboxylic acid methyl ester (1C), as a very hygroscopic, colorless solid, m.p.: 90°–95° C.

20 ml of a ca. 1M solution of lithium hydroxide in water was added to a stirred solution of 3.36 g of 1C in 100 ml of methanol at 0° C., and the mixture was stirred for 1.5 hours at 0° C. The mixture was neutralized (to pH 6–7) with 6N hydrochloric acid, the filtrate was stripped of solvent under reduced pressure and a temperature up to 55° C., and the residue was subjected to very low pressure (<1 Torr.). The residue was dissolved in 75 ml of methanol, 100 ml of ethyl acetate was added, the mixture was filtered, and the solvents were evaporated under reduced pressure. The residue was purified by flash chromatography, using a 2:1 v:v mixture of ethyl acetate and methanol as eluent. The solvents were evaporated and the residue was recrystallized from ethanol/ether, to give N-(N-carbobenzyloxy-L-seryl)-3-azetidinecarboxylic acid (1D) as a colorless hygroscopic solid, m.p.: 138°–143° C.

A solution of 1.57 g of 1D in 150 ml of methanol containing 0.40 g of palladium-on-carbon catalyst was hydrogenated (50 p.s.i.) in a Parr shaker overnight. The mixture was filtered and the methanol was evaporated from the filtrate under reduced pressure. The residue was dissolved in 100 ml of water, the solution was washed with ethyl acetate, the water was evaporated under reduced pressure, and the residue was subjected to very low pressure (<1 Torr.) and then recrystallized from methanol/ether to give 1, as a colorless solid, m.p.: 192°–193° C.

EXAMLE 2

Demonstration of Selective Pollen Sterilization

Plants of spring wheat (*Triticum aestivum* cv. Yecora rojo) were grown in pots (four plants per pot) in a greenhouse under controlled conditions for optimum growth. The compound was applied as an aqueous solution containing 0.75% Tween 20 as surfactant, at the rate of 600 liters per hectare. Control plants were sprayed with water containing 0.75% Tween 20. The compound was applied at dosages of 1 and 2 kilograms per hectare, and was applied to the plants during spike development prior to head emergence. The stage of development (length of spike primordia) was determined by measuring the lengths of a random sampling of five spikes. All were in the range of 3.5 to 4.0 centimeters in length (stages 33–43, Zadok's scale).

After treatment, the plants were placed in a randomized block arrangement, with at least four replicates per treatment and two controls per replicate.

As the spikes emerged, the mainstem of each of the four plants was bagged to prevent cross-pollination. This test determined the overall effect of the test compound upon the flowers of the plants, based upon self-pollination. To determine that the effect was selective, with respect to the male parts only, in some cases, half (i.e., two) of the mainstem spikes per pot were hand-crossed with pollen from untreated plants. Control spikes also were hand-crossed.

When the developing seeds reached the soft dough stage, water was withheld, to dry the seeds for harvest, and the number of seeds that had been set were counted. The following results were obtained.

TABLE 1

| Rate (kg/ha) | Head Description | Seed Set (Percent Compared to the Control) |
|---|---|---|
| 1 | Main Stem | 76 |
|   | Cross-pollinated | 130 |
| 2 | Main Stem | 30 |
|   | Cross-pollinated | 110 |

We claim:

1. A compound of the formula:

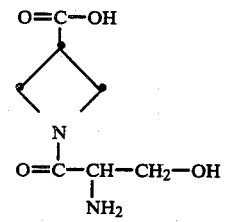

2. A method for sterilizing the male parts of a wheat plant, which comprises applying to the plant prior to pollen shed an effective dosage of the compound of claim 1.

3. A composition of matter adapted for sterilizing the male parts of a wheat plant, said composition comprising an effective amount of the compound of claim 1 together with an inert carrier and a surface-active agent.

4. A composition of matter according to claim 3 wherein the carrier is water and the surface-active agent is a nonionic material.

5. A method for producing hybrid wheat seed which comprises applying to a candidate female parent wheat plant prior to pollen shed an effective dosage of the compound of claim 1, causing the candidate female wheat plant to be pollinated with pollen from a candidate male parent wheat plant, allowing the female parent to mature until the seed is mature, and harvesting the seed.

* * * * *